(12) United States Patent
Joguparthi et al.

(10) Patent No.: US 11,826,322 B2
(45) Date of Patent: Nov. 28, 2023

(54) PRE-FILLED SYRINGE

(71) Applicant: Teva Pharmaceuticals USA, Inc., North Wales, PA (US)

(72) Inventors: Vijay Joguparthi, Khammam (IN); Rosario LoBrutto, Monroe, NY (US)

(73) Assignee: Teva Pharmaceuticals USA, Inc., North Wales, PA (US)

( * ) Notice: Subject to any disclaimer, the term of this patent is extended or adjusted under 35 U.S.C. 154(b) by 554 days.

(21) Appl. No.: 16/998,559

(22) Filed: Aug. 20, 2020

(65) Prior Publication Data
US 2020/0375922 A1 Dec. 3, 2020

Related U.S. Application Data

(62) Division of application No. 15/405,877, filed on Jan. 13, 2017, now Pat. No. 10,835,503.

(51) Int. Cl.
*A61K 31/137* (2006.01)
*C09J 175/16* (2006.01)
(Continued)

(52) U.S. Cl.
CPC ............ *A61K 31/137* (2013.01); *A61K 47/02* (2013.01); *A61L 31/022* (2013.01); *A61L 31/026* (2013.01);
(Continued)

(58) Field of Classification Search
CPC ...... A61K 31/137; A61K 47/02; A61K 47/12; A61K 9/0019; A61L 31/022;
(Continued)

(56) References Cited

U.S. PATENT DOCUMENTS 6,488,668 B1 * 12/2002 Prindle .............. A22C 17/0053
128/898
9,283,197 B1 * 3/2016 Taneja ................. A61K 31/137
(Continued)

FOREIGN PATENT DOCUMENTS

CN 104434239 3/2015
DE 10252838 6/2004
(Continued)

OTHER PUBLICATIONS

International Preliminary Report On Patentability corresponding to International Patent Application No. PCT/IB2018/050175, dated Jul. 16, 2019;12 pages.
(Continued)

*Primary Examiner* — Brandy S Lee
(74) *Attorney, Agent, or Firm* — Blank Rome LLP

(57) ABSTRACT

The invention relates to a pre-filled syringe, an auto-injector device comprising such pre-filled syringe, a method of administering a pharmaceutical composition with such auto-injector device, and a manufacturing method for such auto-injector device. The pre-filled syringe comprises a container and a needle. The container is filled with a pharmaceutical composition comprising epinephrine, a buffer, and water. The buffer is configured to buffer in a pH range between 3 and 4. The needle is adhered to the container by means of a urethane acrylate or urethane methacrylate acrylic light cure adhesive, which is configured to provide a pull out resistance of the needle relative to the container which is between 30 N to 100 N, preferably between 50 N to 70 N, more preferably greater than 60 N after 90 days exposure to the pharmaceutical composition at 40° C. and 75% relative humidity (RH). In an example, the pharmaceutical composition is for the treatment of an anaphylactic event.

27 Claims, 4 Drawing Sheets

(51) Int. Cl.
| | |
|---|---|
| *A61K 47/02* | (2006.01) |
| *A61L 31/02* | (2006.01) |
| *A61L 31/04* | (2006.01) |
| *A61L 31/16* | (2006.01) |
| *A61M 5/20* | (2006.01) |
| *A61M 5/31* | (2006.01) |
| *A61M 5/315* | (2006.01) |
| *A61M 5/32* | (2006.01) |
| *A61M 5/34* | (2006.01) |
| *C09J 175/04* | (2006.01) |
| *B65B 3/00* | (2006.01) |
| *A61K 9/00* | (2006.01) |
| *B65B 55/14* | (2006.01) |
| *A61K 47/12* | (2006.01) |

(52) U.S. Cl.
CPC ............ *A61L 31/048* (2013.01); *A61L 31/16* (2013.01); *A61M 5/2033* (2013.01); *A61M 5/3129* (2013.01); *A61M 5/31591* (2013.01); *A61M 5/3243* (2013.01); *A61M 5/349* (2013.01); *C09J 175/16* (2013.01); *A61K 9/0019* (2013.01); *A61K 47/12* (2013.01); *A61M 5/329* (2013.01); *A61M 2005/2026* (2013.01); *A61M 2205/02* (2013.01); *A61M 2207/00* (2013.01); *B65B 3/003* (2013.01); *B65B 55/14* (2013.01); *C09J 175/04* (2013.01)

(58) Field of Classification Search
CPC ...... A61L 31/026; A61L 31/048; A61L 31/16; A61M 2005/2026; A61M 2205/02; A61M 2207/00; A61M 5/2033; A61M 5/3129; A61M 5/31591; A61M 5/3243; A61M 5/329; A61M 5/349; B65B 3/003; B65B 55/14; B65B 55/16; B65B 7/2821; C09J 175/04; C09J 175/16

See application file for complete search history.

(56) References Cited

U.S. PATENT DOCUMENTS

| | | |
|---|---|---|
| 2007/0148326 A1 | 6/2007 | Hastings |
| 2008/0086107 A1 | 4/2008 | Roschak |
| 2012/0101475 A1* | 4/2012 | Wilmot ............... A61M 5/2033 604/506 |
| 2014/0323986 A1* | 10/2014 | Skufca .................. A61M 5/349 432/9 |
| 2016/0058715 A1* | 3/2016 | Rakesh .................... A61K 9/08 206/364 |
| 2016/0114110 A1 | 4/2016 | Kerns |

FOREIGN PATENT DOCUMENTS

| | | |
|---|---|---|
| EP | 1640008 | 3/2006 |
| EP | 2123307 | 11/2009 |
| WO | 0240087 | 5/2002 |
| WO | 20100139751 | 12/2010 |
| WO | 2014057365 | 4/2014 |
| WO | 20140127015 | 8/2014 |

OTHER PUBLICATIONS

International Search Report corresponding to International Patent Application No. PCT/IB2018/050175, dated Apr. 17, 2018; 6 pages.

* cited by examiner

PRE-FILLED SYRINGE

CROSS-REFERENCE TO RELATED PATENT APPLICATIONS

This application is a divisional of U.S. patent application No. 15/405,877, filed Jan. 13, 2017, which is hereby incorporated by reference in its entirety.

FIELD OF THE INVENTION

The invention relates to a pre-filled syringe, an auto-injector device comprising such syringe, a method of administering a pharmaceutical composition with such auto-injector device, and a manufacturing method for such auto-injector device.

BACKGROUND OF THE INVENTION

There are pre-filled syringes available, but in particular syringes pre-filled with epinephrine may be further improved. The improvement may be in particular directed to an increased shelf life of the pre-filled syringe containing epinephrine.

SUMMARY OF THE INVENTION

Hence, there may be a need to provide a syringe pre-filled with epinephrine, which enables an increased shelf life.

The problem of the present invention is solved by the subject-matter of the independent claims, wherein further embodiments are incorporated in the dependent claims. It should be noted that the aspects of the invention described in the following apply also to the pre-filled syringe, the auto-injector device comprising such syringe, the method of administering a pharmaceutical composition with such auto-injector device, and the manufacturing method for such auto-injector device.

According to the present invention, a pre-filled syringe is presented. The pre-filled syringe may be used for immediate self-administration as emergency treatment of allergic reactions (Type I, including anaphylaxis to stinging insects) delivering 0.15 mg and 0.3 mg of epinephrine at concentrations of 0.5 mg/mL and 1.0 mg/mL, respectively, as sterile solution for single use injection by means of an auto-injector. Epinephrine is also known as adrenaline. There may be two types of auto-injectors available, one for junior (pediatric) and one for adult administration. Both auto-injectors may be suitable for intramuscular or subcutaneous administration and for easy use by the lay person as first aid.

The pre-filled syringe according to the present invention comprises a container and a needle. The container is filled with a pharmaceutical composition comprising epinephrine, a buffer, and water. The buffer is configured to buffer in a pH range between 3 and 4. The needle is adhered to the container by means of a urethane acrylate or urethane methacrylate acrylic light cure adhesive, which is configured to provide a pull out resistance of the needle relative to the container between 30 N to 100 N, preferably between 50 N to 70 N, more preferably greater than 60 N after 90 days exposure to the pharmaceutical composition at 40° C. and 75% relative humidity (RH). The pull out resistance is defined the force required to dislodge the needle from the syringe, in particular dislodge a bonded stainless steel needle from a glass container.

In other words, the pre-filled syringe according to the invention comprises epinephrine and a buffer configured to buffer in a pH range between 3 and 4 to minimize degradation reactions and to thereby keep the composition stable, and a needle adhered to a container by means of a urethane acrylate or urethane methacrylate acrylic light cure adhesive configured to keep above defined pull out resistance stable. As a synergetic effect, the stable composition avoids more severe attacks of the composition on the adhesive and the stable adhesive avoids more severe attacks of the surrounding oxygen on the composition. Consequently, the shelf life of the pre-filled syringe is greatly increased.

The very complex interdependences between the components of the pharmaceutical composition, the pH range, the urethane acrylate or urethane methacrylate acrylic light cure adhesive and the pull out resistance will be explained in much detail in the following:

The Components of the Pharmaceutical Composition and the pH Range

Epinephrine is chemically unstable in aqueous solution and undergoes a variety of degradation reactions such as racemization, oxidation, photodegradation, hydrolysis, and substitution reactions. The rates of these multiple degradation reactions depend on the complex interplay of pH, dissolved oxygen available bisulfites and light. The multiple degradation pathways may occur consecutively and in parallel.

The major degradation routes of the pharmaceutically more potent L-adrenaline are oxidation, racemization and sulfonation by additives such as sodium metabisulfite employed as an antioxidant. The products of these reactions, such as D-adrenaline, L- or D-adrenaline sulfonate, leucoadrenochrome or adrenochrome possess little or no pharmacological activity compared with the parent L-adrenaline compound. Epinephrine racemization occurs easily in acidic solutions. Rapid oxidation of epinephrine (in aqueous solutions without antioxidant) results in strongly colored, pharmacologically inactive degradation products. Accordingly, antioxidants may have to be used in the injectable formulations. As the kinetics of racemization decreases and oxidation increase with increasing the solution pH, there is an optimum pH range at which racemization and oxidation are balanced to minimize these degradation routes. Incorporation of a buffer configured to buffer in a pH range between 3 and 4 is useful to control the pH within a narrow range.

As a result, the pharmaceutical composition in the pre-filled syringe according to the invention comprises epinephrine and the buffer configured to buffer in a pH range between 3 and 4 to keep the composition stable.

The Urethane Acrylate or Urethane Methacrylate Acrylic Light Cure Adhesive

The pharmaceutical composition further influences the mechanical connection between the container and the needle. The pre-filled syringe comprises a cylindrical syringe container made of glass or plastic with an injection needle attached thereto. A typical process for the manufacture of pre-filled syringes includes the steps of arranging the needle in a reception channel of the container and fixing the needle to the container by use of radiation-curable adhesives, e.g. by UV-irradiation. In an additional step, the syringes might be cleaned with hot water at about 70° C. Further manufacturing steps may include siliconization and a couple of sterilization cycles, e.g. 1-3 cycles of ethylene oxide (ETO) sterilization and filling with the drug formulation injectable product.

At an inner boundary between needle and inner container, the epinephrine drug formulation might be in direct contact with and/or exposed to the adhesive. In syringes pre-filled with e.g. drug excipients such as buffers, antioxidants or tonicity agents, leachables/extractables may dissolve from and/or diffuse out of the adhesive leading to or increasing degradation of the drug product upon storage over long periods of time and/or at elevated temperatures and/or elevated relative humidity (e.g. 40° C. and 75% relative humidity (RH)).

Conversely, drug components such as buffers, antioxidants or tonicity agents may dissolve and/or diffuse into the adhesive leading to degradation of the adhesive by components of the pharmaceutical composition. This degradation may lead to a decrease of bonding strength between needle and container, thus the pull out resistance of the needle relative to the container over the lifetime or shelf life of the pre-filled syringe may significantly decrease. The decrease of the pull out resistance may lead to a detrimental detachment or weakening, breakage of the bond between needle and container while, for example, being pushed with force through clothes and into the skin for an emergency injection. The needle may dislodge early or bend during injection resulting in thigh aceration.

To avoid such degradation of the mechanical connection between the container and the needle, the use of a urethane acrylate or urethane methacrylate acrylic light cure adhesive is presented, which is configured to provide a pull out resistance of the needle relative to the container which is between 30 N to 100 N, preferably between 50 N to 70 N, and more preferably greater than 60 N after 90 days exposure to the pharmaceutical composition at 40° C. and 75% relative humidity (RH).

Examples for such adhesives for stainless needle-glass container bonding are one component heat cured epoxy based structural adhesives. Such epoxy based structural adhesives, e.g. Loctite 9535, show a superior tensile bonding strength in the range of at least 30-40 N/mm$^2$. Other examples for such adhesives for stainless needle-glass container bonding are two component epoxy resin structural adhesives such as Loctite M-21HP, also having a superior tensile bonding strength above 50 N/mm$^2$.

Other examples for such adhesives for stainless needle-glass container bonding are fast-curing, in particular radiation curing adhesives, typically light- or photo-curing adhesives, such as acrylate-based adhesives, which can be cured by visible light or UV-light. A chemical type acrylate of this class is Loctite 3011 having a tensile bonding strength in the range of 1-5 N/mm$^2$.

Urethane acrylate or urethane methacrylate acrylic light cure adhesives can comprise additives such as fill materials and/or a toughening agents, tonics, stabilizers, initiators, antipolymering agents. In urethane acrylate or urethane methacrylate acrylic light cure adhesives, urethane pre-polymers may be end capped with hydroxyl acrylates and/or methacrylates to build an urethane acrylate or urethane methacrylate oligomer.

Further suitable examples for light cure adhesives for bonding stainless steel needles to glass or plastic containers are modified acrylates or modified methacrylates, comprising an acrylic and/or methacrylic monomer and additives such as fill materials and/or a toughening agents, tonics, stabilizers, initiators, anti-polymerization agents. Such modified acrylates may comprise at least one acrylic monomer or component such as N,N-dimethylacrylamine, 2-ethoxayethyl acrylate, 2-hydroxylethyl actrylate, 2-phenoxyethyl acrylate, butyl acrylate, acrylic acid, cyclohexyl acrylate, dicyclopentenyl acrylate, dodecyl acrylate, ethyl acrylate, hydroxylethyl acrylate, methacrylamide, methacrylic acid, methyl acrylate, neopentyl glycol diacrylate, norbonyl diacrylate, phenyl acrylate, triethylene, trimethoxysilyloxypyropyl acrylate and others. Such modified methacrylates may comprise at least one methacrylic monomer or component such as 2-methylcylohexyl methacrylate, benzyl methacrylate, butyl, methacrylate, cylohexyl methacrylate, ethoxylated bisphenol A dimethacrylate, ethylene glycoldimethacrylate, hexyl methacrylate, isopropyl methacryklate, methyl, methacrylate, neopentyl methacrylate, phenyl methacrylate, tetraahydrofufuryl methacrylate, triethylene glycol dimethacrylate and others. Such additives being designed to increase tensile strength and/or glass temperature $T_G$ for improving steam sterilization stability and/or better acidic resistance.

An example of a modified acrylate light cure adhesive is Loctite AA 3081. This UV-light curable modified acrylate shows a tensile bonding strength above 20-30 N/mm$^2$ (lower value break strength, higher value yield strength) and an excellent bond strength retention after being subjected to standard sterilization methods, such as steam vapor autoclave, EtO and Gamma Radiation (25 to 50 kiloGrays cumulative).

An example of a urethane methacrylate acrylic light cure adhesive is Loctite 3345. Loctite 3345 shows a low to medium tensile bonding strength above 7 N/mm$^2$ for steel to glass bonding. According to the product description/sheet, products similar in composition to Loctite 3345 subjected to standard sterilization methods, such as EtO and Gamma Radiation (25 to 50 kiloGrays cumulative), show excellent bond strength retention. Loctite 3345 should maintain bond strength after 1 cycle of steam autoclave.

Modified acrylate or modified methacrylate acrylic light cure adhesives, such as Loctite AA 3081 show a superior tensile bonding strength compared to urethane acrylate or urethane methacrylate acrylic light cure adhesives such as Loctite 3345 (above 20-30 N/mm$^2$ compared to above 7 N/mm$^2$). In addition, modified acrylate or modified methacrylate acrylic light cure adhesives are less sensitive to heat/humidity. Surprisingly, urethane acrylate or urethane methacrylate acrylic light cure adhesives show a much better pull out resistance preservation when exposed to a pharmaceutical composition comprising epinephrine, a buffer and water, when the buffer is configured to buffer in a pH range between 3 and 4.

As a result, the pre-filled syringe according to the invention comprises a stainless steel needle adhered to a glass container by means of a urethane acrylate or urethane methacrylate acrylic light cure adhesive, which is configured to keep above defined pull out resistance stable.

The Pull Out Resistance

The pull out resistance is defined as the force required to dislodge the needle from the syringe, in particular dislodge the bonded stainless steel needle from the glass container. In an example, the pull out resistance is between 30 N and 100 N after 90 days exposure to the pharmaceutical composition at 40° C. and 75% relative humidity (RH). In an example, the pull out resistance is between 50 N and 70 N after 90 days exposure to the pharmaceutical composition at 40° C. and 75% relative humidity (RH). In an example, the pull out resistance is greater than 60 N after 90 days exposure to the pharmaceutical composition at 40° C. and 75% relative humidity (RH). In an example, the pull out resistance is about 60 N after 90 days exposure to the pharmaceutical composition at 40° C. and 75% relative humidity (RH).

In summary, the pre-filled syringe according to the invention comprises epinephrine and the buffer configured to buffer in a pH range between 3 and 4 to keep the composition stable, and the stainless steel needle adhered to the glass container by means of the urethane acrylate or urethane methacrylate acrylic light cure adhesive configured to keep above defined pull out resistance stable. As a synergetic effect, the stable composition avoids more severe attacks of the composition on the adhesive and the stable non decomposing adhesive avoids more severe attacks of the surrounding oxygen on the composition. Consequently, the shelf life of the pre-filled syringe is greatly increased.

The Needle

The acid pharmaceutical composition may in addition negatively influence the material of the stainless steel needle leading again to a reduced lifetime or shelf life of the pre-filled syringe. The negative influence may be corrosion, in particular pitting or intercrystalline corrosion and/or a decrease in mechanical strength. To avoid such negative influences and to increase the corrosion resistance, the stability of mechanical strength and/or the shelf life, in an example, the needle is made from high corrosion resistance steel comprising 15 to 20% Cr, 8 to 16% Ni and 1 to 4% Mo. For the same reasons, in another example, the needle is made from high corrosion resistance steel comprising 15 to 25% Cr, 20 to 30% Ni and 3 to 6% Mo.

Needles in a range from 19 G to 25 G may be used for injection of the epinephrine formulation. Needles from 22 G to 25 G are preferred for the pediatric injection. In a most preferred example, a 22 G standard size needle having an outer diameter between 0.69 to 0.74 mm and an inner diameter between 0.39 to 0.45 mm is used. To decrease injection time or to decrease injection pain (decrease of pain by decrease of outer diameter), a thin wall needle or a special thin wall, ultra-thin wall needle might be used. As the needle is used for intramuscular injection, the needle length should be in the range between 0.8 inch to 1.5 inch, respective 20.3 mmm to 38.1 mm for adult injection and between ⅞ inch to 1.25 inch, respective 22.2 mm to 31.75 mm for pediatric injection. In a most preferred example, the needle length is between 20 mm to 25 mm. In an autoinjector, the needle is partially covered and captured by an autoinjector housing. The exposed needle length, as measured from a skin contact to a face of the autoinjector, is between 13 mm to 17 mm 15 mm+/−2 mm for the adult injection autoinjector and 13 mm+/−2 11 mm to 15 mm for the pediatric injection autoinjector.

The Container

Two dimensions affect dose accuracy of the pre-filled syringe, namely a length of a ram of the syringe and a position of a stopper in the container. In addition, a process of inserting the stopper into the container determines a headspace volume in the syringe which again affects the dose accuracy. The term "headspace" refers to the gas space above the product in the container. So to improve a dose accuracy, above mentioned dimensions of syringe and stopper (diameter and length) must be within predetermined tolerances as well as a process of filling the syringe and inserting the stopper must be carefully controlled. Based on all possible tolerances and process parameters, the best dose accuracy can be achieved with a slightly overfilled syringe. Therefore in an example, the container contains between 0.95 ml and 1.07 ml and preferably between 1.04 and 1.07 ml of the pharmaceutical composition.

Options Concerning the Pharmaceutical Composition

In an example, the epinephrine content is between 0.9 and 1.1 mg/mL for adult patients or between 0.4 and 0.6 mg/mL for pediatric patients. The pharmaceutical composition may further comprise sodium chloride for tonicity adjustment, sodium metabisulfite (SMBS) as an antioxidant agent, hydrochloric acid as pH adjuster, sodium tartrate as buffering agent, and water for injection as diluent. The addition of tartrate buffer and a low concentration of antioxidant enhances the stability of the formulation without impacting safety and efficacy.

The addition of a buffer as described in the following may enhance the stability of the formulation without impacting safety and efficacy. In an example, the buffer is configured to buffer at a pH of about 3.4 to 4.0 In an example, the buffer is a carboxylic acid. In an example, the buffer is a bicarboxylic acid. In an example, the buffer is a tartrate salt. In an example, the buffer is sodium tartrate dihydrate.

In an example, the sodium tartrate dihydrate content is between 1.0 and 1.6 mg/mL for adult patients or between 0.5 and 0.8 mg/mL for pediatric patients. In an example, the sodium tartrate dihydrate content is about 1.38 mg/mL for adult patients or about 0.69 mg/mL for pediatric patients.

Also the addition of an antioxidant and its low concentration may enhance the stability of the formulation without impacting its safety and efficacy. In an example, the pharmaceutical composition further comprises an antioxidant. In an example, the antioxidant content in the pharmaceutical composition is below 1.6 mg/mL. In an example, the antioxidant is sodium metabisulfite. In an example, the sodium metabisulfite content is between 1.1 and 1.3 mg/mL. In an example, the sodium metabisulfite content in the pharmaceutical composition is about 1.2 mg/mL.

In an example, the pharmaceutical composition further comprises a pH adjuster. In an example, the pH adjuster is hydrochloric acid.

In an example, the pharmaceutical composition further comprises a tonicity adjuster. In an example, the tonicity adjuster is a sodium chloride.

According to the present invention, also an auto-injector device is presented. The auto-injector device comprises a syringe and a firing mechanism. The syringe comprises a needle and a container. The container is filled with a pharmaceutical composition comprising epinephrine, a buffer, and water. The buffer is configured to buffer in a pH range between 3 and 4. The needle is adhered to the container by means of a urethane acrylate or urethane methacrylate acrylic light cure adhesive, which is configured to provide a pull out resistance of the needle relative to the container between 30 N to 100 N, preferably between 50 N to 70 N, more preferably greater than 60 N after 90 days exposure to the pharmaceutical composition at 40° C. and 75% relative humidity (RH). The firing mechanism is configured to expel the pharmaceutical composition from the syringe and to inject it into a subject.

There may be two types of auto-injectors available, one for junior (pediatric) and one for adult administration. Both auto-injectors may be suitable for intramuscular or subcutaneous administration. In an example, the pressure during injection into the subject is in a range of 100 to 4000 psi. In an example, the syringe provides about 1 mL of the pharmaceutical composition and the auto-injector device is configured to deliver 0.3 ml of the pharmaceutical composition during a single injection in below 0.5 sec, in particular between 0.1 sec and 0.3 seconds.

In an example, it was determined whether both auto-injectors, one for junior (pediatric) 0.15 mg one for adult administration 0.3 mg strengths are equivalent with respect to the volume of drug that is delivery after actuating a device. The statistical analysis results show strong equivalence compared to an allowed equivalence range of 0.251 ml to 0.349 ml.

In another example a second analysis has been done for comparing two sublots for 0.15 mg strength from the same 100 L compounded solution that were filled using same processing conditions, fill volume and vacuum pressure but filled at different time interval.

The individual delivered volume of the epinephrine formulation after actuation in any of the above examples is in between 0.250 ml and 0.349 ml (nominal 0.300 ml), preferably in between 0.27 ml to 0.32 ml (n>50 tested PFS epinephrine formulation autoinjector deliveries).

The arithmetic mean of delivered volume of the epinephrine formulation after actuation in any of the above examples is in between 0.295 ml (95% Lower Confidence Interval for Mean, n>50 tested PFS epinephrine formulation autoinjector deliveries) to 0.305 ml (95% Upper Confidence Interval for Mean, n>50 tested PFS epinephrine formulation autoinjector deliveries).

The auto-injector device and the firing mechanism are further described with respect to the drawings.

According to the present invention, also a method of administering a pharmaceutical composition with an auto-injector device is presented. It comprises the following steps:

a) Providing an auto-injector device comprising a syringe and a firing mechanism. The syringe comprises a needle and a container. The container is filled with a pharmaceutical composition comprising epinephrine, a buffer and water. The buffer is configured to buffer in a pH range between 3 and 4. The needle is adhered to the container by means of a urethane acrylate or urethane methacrylate acrylic light cure adhesive, which is configured to provide a pull out resistance of the needle relative to the container between 30 N to 100 N, preferably between 50 N to 70 N, more preferably greater than 60 N after 90 days exposure to the pharmaceutical composition at 40° C. and 75% relative humidity (RH).

b) Activating the firing mechanism to expel the pharmaceutical composition from the syringe and to inject it into a subject.

The method of administering the pharmaceutical composition with the auto-injector device is further described with respect to the drawings. In an example, the pharmaceutical composition is for the treatment of an anaphylactic event. The active ingredient of the pharmaceutical composition is epinephrine also known as adrenaline. It is the drug of choice for the emergency treatment of severe allergic reactions (Type I) due to insect stings or bites, foods, drugs and other allergens. It can also be used in the treatment of anaphylaxis of unknown cause (idiopathic anaphylaxis) or exercise-induced anaphylaxis.

According to the present invention, also a manufacturing method for an auto-injector device is presented. It comprises the following steps:

a) Manufacturing a pharmaceutical composition comprising epinephrine, a buffer and water. The buffer is configured to buffer in a pH range between 3 and 4.

b) Sterilizing the pharmaceutical composition.

c) Filling the pharmaceutical composition in a container of a syringe. The syringe further comprises a needle. The needle is adhered to the container by means of a urethane acrylate or urethane methacrylate acrylic light cure adhesive, which is configured to provide a pull out resistance of the needle relative to the container between 30 N to 100 N, preferably between 50 N to 70 N, more preferably greater than 60 N after 90 days exposure to the pharmaceutical composition at 40° C. and 75% relative humidity (RH).

d) Assembling the syringe into an auto-injector device which comprises a firing mechanism. The firing mechanism is configured to expel the pharmaceutical composition from the syringe and to inject it into a subject.

The solution may be protected from light during compounding and filling and assembly into devices. The protection from light may be ensured by operating under filtered (amber coloured) light and other light protective mechanisms during the respective processes.

In an example, the manufacturing of the pharmaceutical composition comprises the following steps:
- preparing a solution comprising the buffer and an antioxidant,
- adding a pH adjuster to adjust a pH range of the solution between 2.5 and 4.3,
- adding epinephrine, and
- adding a pH adjuster to adjust a pH range of the solution comprising epinephrine between 3 and 4.

In an example, the pH adjuster is added to adjust a pH value of the solution comprising epinephrine to about 3.4 to 4.0.

In an example, the manufacturing of the pharmaceutical composition comprises the further steps of:
- degassing water, and
- adding the degassed water to the solution comprising epinephrine.

Degassed water for injection may be used to minimize a level of dissolved oxygen to protect the solution during compounding and filling from dissolved oxygen. In an example, the degassing of water comprises the steps of a) subjecting water to vacuum, b) sparging the water with nitrogen gas, and c) again subjecting the water to vacuum. In an example, the water is subjected to vacuum for about 45 minutes in step a) and in step c). In an example, the water is sparged with nitrogen gas at a minimum of 4 L/min for about 120 minutes.

In an example, the sterilizing of the pharmaceutical composition comprises an aseptic filtration. In an example, the aseptic filtration is done at room temperature by means of a polyvinylidenfluoride filter. In an example, the filter has a pore size in the range of 0.1 to 0.3 μm.

As epinephrine degradation may be facilitated by the presence of oxygen in a headspace of the syringe container, this risk may be reduced by adjusting a stopper placement to an optimum stopper height and lower headspace z using vacuum stoppering. The term "headspace z" refers to the gas space above the product in a container. In an example, the filling of the pharmaceutical composition in the syringe (with needle guard) is done through an opening.

Term Definitions

The term "epinephrine" refers to 4-[(1R)-1-Hydroxy-2-(methylamino)ethyl]-1,2-benzenediol, which is produced in the adrenal medulla and which is an endogenous catecholamine which acts directly on both alpha and beta adrenergic receptors. When used in pharmaceutical compositions, epinephrine can act as a non-selective alpha and beta adrenergic agonist and can work rapidly to improve breathing, stimulate the heart, raise dropping blood pressure, reverse hives, and reduce swelling of the face, lips, and throat. Uses for epinephrine include emergency treatment of allergic reactions (Type 1), including anaphylaxis, induction and maintenance of mydriasis during intraocular surgery, treatment of bronchospasm, sensitivity reactions, cardiac arrhythmias, GI and renal hemorrhage, superficial bleeding, premature labor, hypoglycemia, and cardiogenic, hemorrhagic, and traumatic shock. Epinephrine can also be used to increase blood flow in advanced cardiac life support (ACLS)

during Cardiac-Pulmonary Resuscitation (CPR), as an adjunct to local anesthesia, and for radiographic uses. The concentration of epinephrine within the pharmaceutical composition for administration to adult patients is 0.7 to 1.5 mg/ml, preferably 0.8 to 1.3 mg/ml, more preferably 0.9 to 1.1 mg/ml and most preferably it is 1.0 mg/ml. The concentration of epinephrine within the pharmaceutical composition for administration to pediatric patients is 0.2 to 0.8 mg/ml, preferably 0.3 to 0.7 mg/ml, more preferably 0.4 to 0.6 mg/ml and most preferably it is 0.5 mg/ml.

The term "buffer" refers to a component present in a composition or solution which may provide a resistance to a significant change in pH caused by a strong acid or base. A buffer may comprise a single agent or more than one agent, such as a weak acid and its conjugate base. A buffer may provide a resistance to a significant pH change by interacting with a strong acid or strong base in a composition or solution, thereby at least partially preventing the pH of the composition or solution from changing significantly. Generally, a buffer has one or more buffer ranges wherein the buffer has the ability to provide resistance to significant pH change. When a composition or solution comprising the buffer has a pH inside the buffer's buffer range, the pH of the composition or solution will not change significantly with the addition of equimolar amounts of a strong acid or strong base.

The term "antioxidant" refers to a component in a composition that may prevent and/or inhibit the formation of unacceptable amounts of oxidized species in the composition after a certain period of shelf life. In some embodiments, the antioxidant may react with oxygen that might otherwise compromise the composition by producing impurities in the composition. Oxygen may originate from the composition's environment or the composition itself. For example, oxygen may originate from residual oxygen present in the headspace of vials containing the composition. Suitable antioxidants include, but are not limited to, sodium metabisulfite, sodium sulfite, ascorbic acid, cysteine, cystin and glutathione. Preferably, sodium metabisulfite is used as antioxidant.

The term "tonicity" refers to the effective osmotic pressure equivalent of a solution or composition. Further, tonicity is the 'effective osmolality' and is equal to the sum of the concentrations of the solutes which have the capacity to exert an osmotic force across the membrane. A "tonicity adjuster" adjusts the tonicity of a pharmaceutical composition so that it is isotonic with body fluids, in particular blood. Suitable tonicity adjusters include salts such as sodium chloride and potassium chloride and sugars such as mannitol, dextrose, sucrose and trehalose as well as glycerol. Preferably sodium chloride is used as a tonicity adjuster. The concentration of the tonicity adjuster and preferably of sodium chloride is 20 to 200 mM, preferably 40 to 150 mM, more preferably 80 to 120 mM and most preferably 100 mM.

A pH adjuster is an acid or a base which is just to establish a specific pH of the pharmaceutical composition. Suitable acids include hydrochloric acid, acetic acid, citric acid and sodium phosphate.

The term "shelf life" refers to the length of time that a product may be stored without becoming unfit for medical use. Examples of compositions which are unfit for medical use include, but are not limited to, compositions with high impurity levels that are not toxicological qualified and/or the presence of physical changes described herein, such as colour change and/or the presence of insoluble particles.

It shall be understood that the pre-filled syringe, the auto-injector device comprising such syringe, the method of administering a pharmaceutical composition with such auto-injector device, and the manufacturing method for such auto-injector device according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

The invention relates to a pre-filled syringe 10, an auto-injector device 20 comprising such pre-filled syringe 10, a method of administering a pharmaceutical composition with such auto-injector device 20, and a manufacturing method for such auto-injector device 20.

The active ingredient of the present drug product is epinephrine USP also known as adrenaline. It is the drug of choice for the emergency treatment of severe allergic reactions (Type I) due to insect stings or bites, foods, drugs and other allergens. It can also be used in the treatment of anaphylaxis of unknown cause (idiopathic anaphylaxis) or exercise-induced anaphylaxis.

Each auto-injector for adults delivers a single dose of 0.3 mg epinephrine injection, USP, 1:1000 (0.3 mL) in a sterile solution. Each auto-injector for juniors delivers a single dose of 0.15 mg epinephrine injection, USP, 1:2000 (0.3 mL) in a sterile solution. The auto-injectors each contain 1 mL epinephrine solution. Approximately 0.7 mL remains in the auto-injector after activation and cannot be used.

Figure 1:
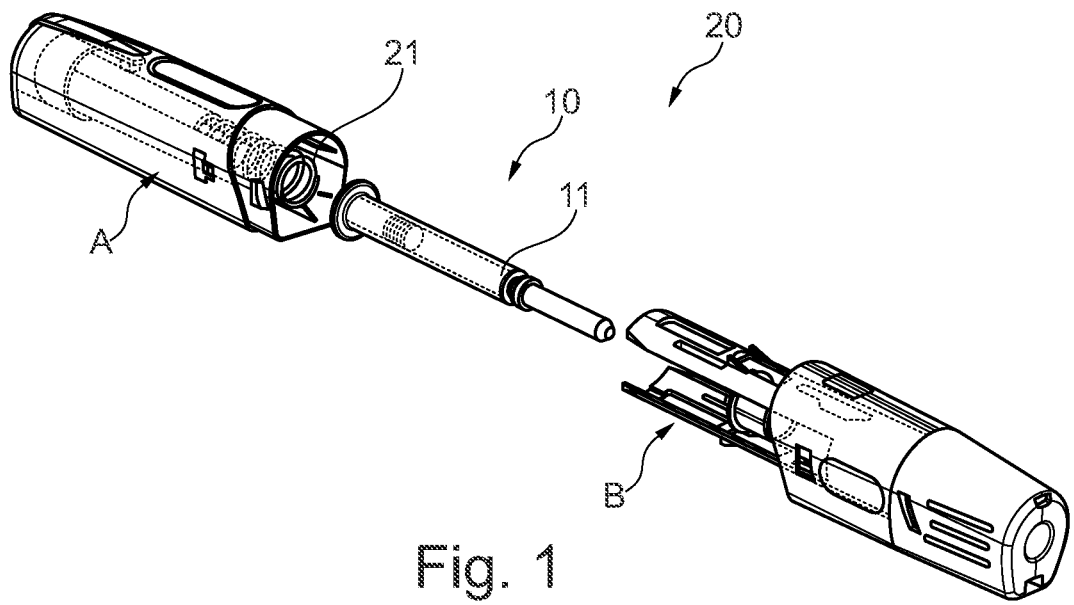
FIG. 1 shows schematically and exemplarily an exploded view of an embodiment of an auto-injector device according to the invention.

FIG. 1 shows schematically and exemplarily an exploded view of an embodiment of an auto-injector device 20 according to the invention for immediate self-administration emergency treatment for allergic reactions (anaphylaxis). The auto-injector device 20 is a single-use, disposable, spring-powered, non-sterilized device for sterile drug delivery. The epinephrine drug product is available in two strengths (junior and adult) with the same auto-injector. Both junior and adult are designed to administer 0.3 mL of epinephrine drug product from the 1.0 mL contents of a pre-filled syringe 10 during a single injection.

There is no drug fluid pathway within the auto-injector device 20; therefore the auto-injector device 20 does not come in contact with the contents of the pre-filled syringe 10. The auto-injector device 20 consists of two sub-assemblies (A-half and B-half) into which a pre-filled syringe 10 is assembled to form a final delivery system.

The auto-injector device 20 comprises a pre-filled syringe 10 and a firing mechanism 21. The pre-filled syringe 10 comprises a needle 12 and a container 11. The container 11 is filled with a pharmaceutical composition comprising epinephrine, a buffer, and water. The buffer is configured to buffer in a pH range between 3.4 to 4.0. The needle 12 is adhered to the container 11 by means of a urethane methacrylate acrylic light cure adhesive, wherein the urethane methacrylate acrylic light cure adhesive is configured to provide a pull out resistance of the needle 12 relative to the container 11 which is greater than 60 N after 90 days exposure to the pharmaceutical composition at 40° C. and 75% RH. The firing mechanism 21 is configured to expel the pharmaceutical composition from the syringe and to inject it into a subject.

Figure 2:
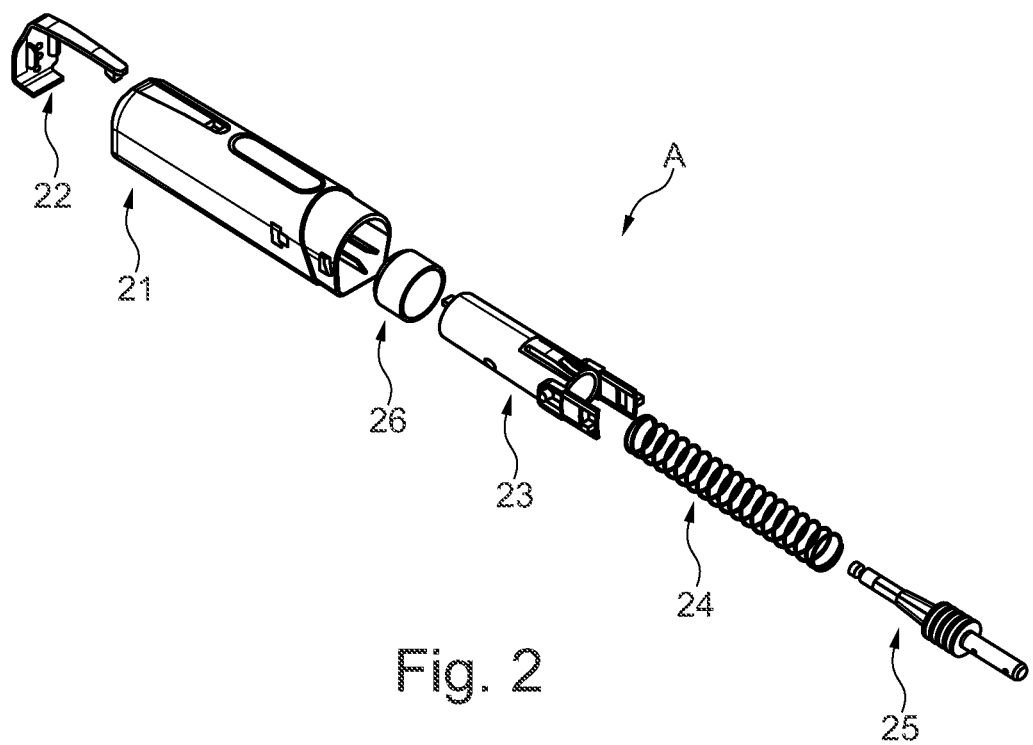
FIG. 2 shows schematically and exemplarily an exploded view of an A-half of the auto-injector device.

FIG. 2 shows schematically and exemplarily an exploded view of the A-half of the auto-injector device 20. The A-half of the auto-injector device 20 comprises a rear housing 21, which contains the components in the A-half sub-assembly and is designed to permanently attach to a B-half front housing 35 via a snap clip. The A-half comprises at least one safety clip 22 onto the back of the rear housing 21, which is removed just prior to the injection. The safety clip 22 thereby prevents inadvertent triggering of the auto-injector device 20 and inadvertent retraction of a needle guard 34 once a safety cap 36 has been removed. The A-half further comprises a latch 23, which houses a main spring 24 and retains a ram 25 so that the main spring 24 is compressed in a preloaded state. The A-half further comprises a trigger 26, which prevents the latch 23 from releasing the ram 25 until the needle guard 34 sufficiently retracts to dislodge the trigger 26; thereby freeing the ram 25 to move under the force of a main spring 24. The retention of the ram 25 is achieved via two prongs that grasp the end of the ram 25, when the trigger 26 is dislodged the prongs release the ram 25. The A-half further comprises the main spring 24, which stores energy in its preloaded state which is used to displace the ram 25 delivering the formulation when the trigger 26 is dislodged by the latch 23. The A-half further comprises the ram 25, which drives a syringe stopper the required distance when the auto-injector device 20 is activated to deliver the formulation to a patient.

Figure 3:
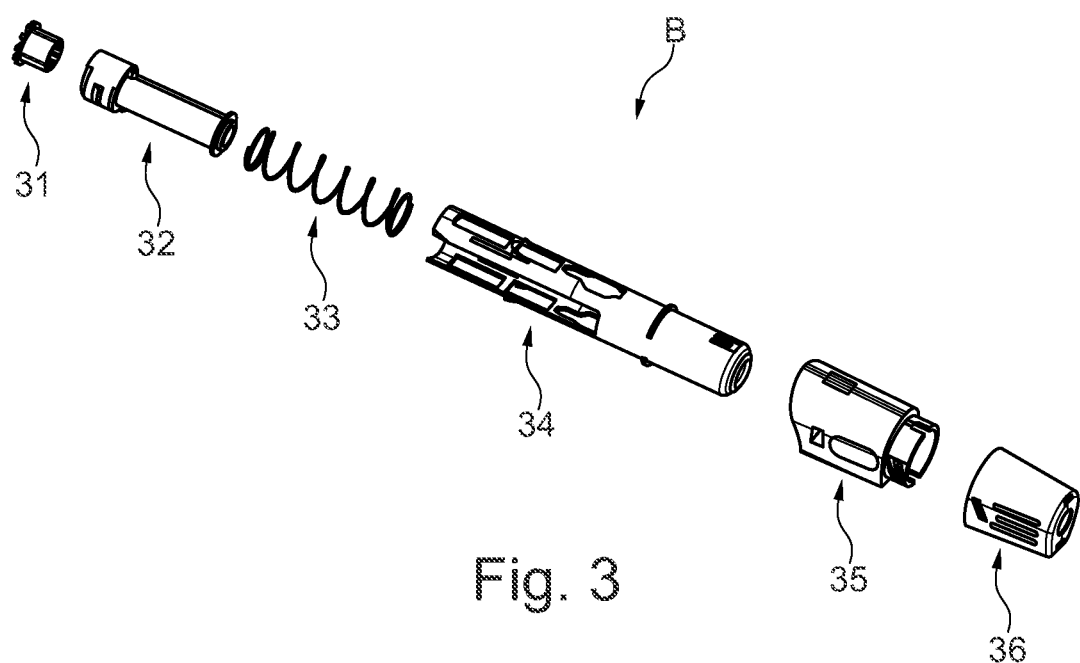
FIG. 3 shows schematically and exemplarily an exploded view of a B-half of the auto-injector device.

FIG. 3 shows schematically and exemplarily an exploded view of the B-half of the auto-injector device 20. The B-half comprises a syringe bushing 31, which removes a clearance between the syringe and a sleeve 32 and compensates for the variability seen in the dimensional characteristics of the glass pre-filled syringe 10. The B-half further comprises the sleeve 32, which locates the syringe within the body of the auto-injector device 20 and mechanically clips to the latch 23 in the A-half assembly. The sleeve 32 has a safety feature, such that if the flanges of the syringe fail, then the safety feature within the sleeve 32 (that is, the sleeve 32 syringe catcher) will retain the syringe to allow correct device operation. The B-half further comprises the return spring 33, which keeps the needle guard 34 in the extended position until an injection is initiated. After the injection has been completed, the return spring 33 then automatically re-extends the needle guard 34, which "locks out" the device; thereby preventing the used syringe needle 12 from being re-exposed. The B-half further comprises the needle guard 34, which protects the pre-filled syringe needle prior to and after the injection. During the injection, the needle guard 34 retracts to expose the needle 12. During activation of the auto-injector device 20, the legs of the needle guard 34 dislodge the trigger 26 and force it away from the latch 23. This allows the force of the main spring 24 to push the ram 25 free of the two prongs on the end of the latch 23; allowing the main spring 24 to drive the ram 25 forward to deliver the contents of the syringe. The B-half further comprises a front housing 35, which contains all of the parts in the B-half sub-assembly and is designed to snap fit with the A-half rear housing 21 after the syringe has been inserted. The front housing 35 has an arrow printed on it with the text "Needle End" to indicate which end the needle 12 comes out of and therefore which end should be applied to the thigh. The B-half further comprises the safety cap 36, which prevents inadvertent retraction of the needle guard 34. When the safety cap 36 is removed, it also removes a needle shield from the syringe (not shown) in preparation for the injection. The safety cap 36 also has an arrow printed on it with the text "Twist" to indicate which direction the safety cap 36 needs to be twisted for removal.

Figure 4:
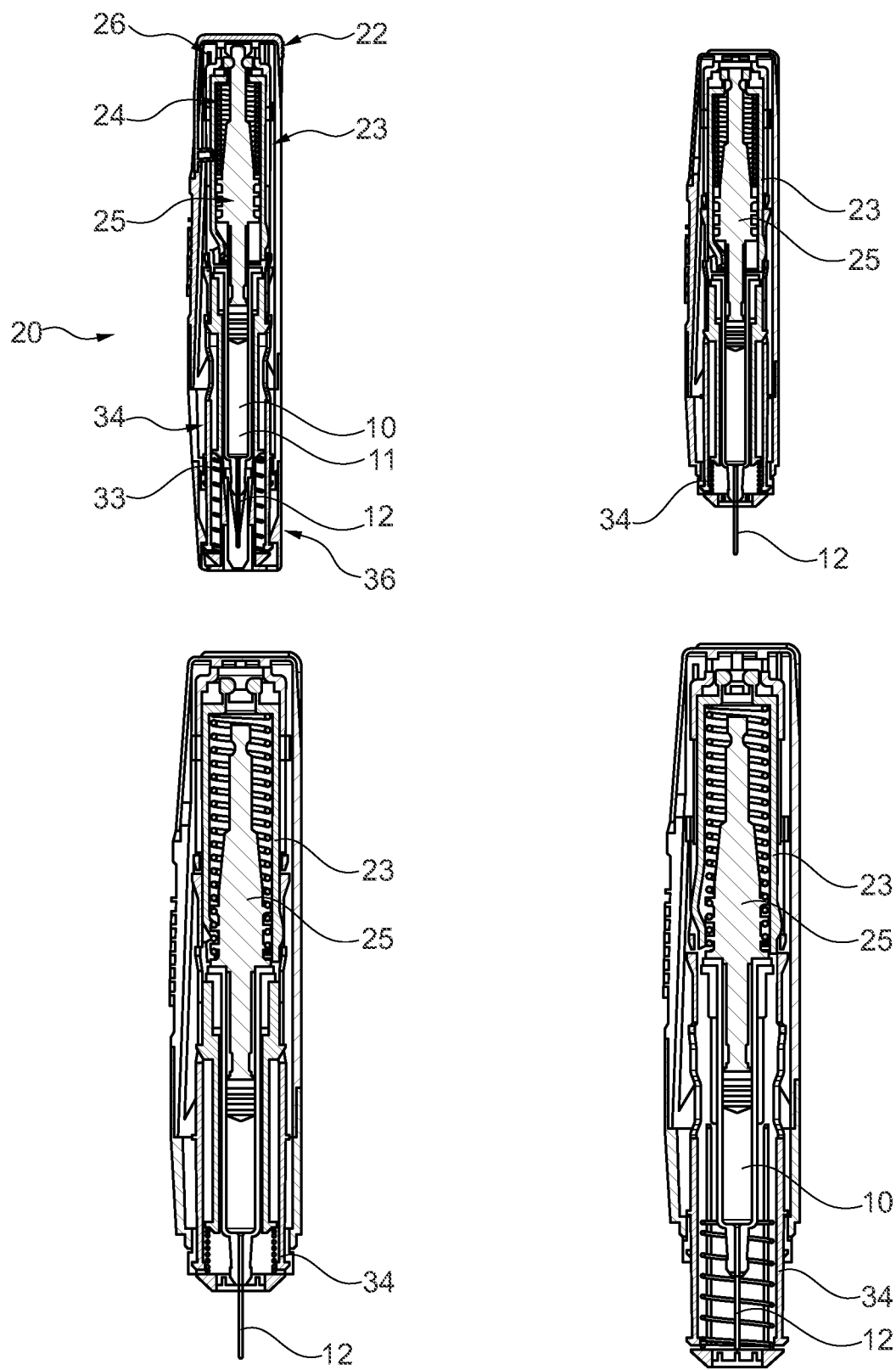
FIG. 4 shows schematically and exemplarily delivery stages for the auto-injector device.

FIG. 4 shows schematically and exemplarily delivery stages for the auto-injector device 20. The auto-injector device 20 is not ready to use when received, as the safety clip 22 and safety cap 36 are in place, as shown in FIG. 4; top left. The safety clip 22 and the safety cap 36 are first removed before the auto-injector device 20 is ready to use. Removal of the safety cap 36 removes the needle shield. The needle guard 34 covers the pre-filled syringe needle 12 and houses the needle shield. The return spring 33 is situated inside the needle guard 34 which extends the needle guard 34 until activation. In the top of the auto-injector device 20, the trigger 26 constrains the latch 23 so that the ram 25 is retained. This prevents the main spring 24 from displacing the ram 25. In this figure, the main spring 24 is in its fully compressed state.

At the start of injection (FIG. 4; top right), the needle guard 34 is fully retracted and the needle 12 exposed. In this position the legs of the needle guard 34 have dislodged the trigger 26, such that the trigger 26 no longer constrains the two prongs of the latch 23. The two prongs sit in an indentation groove at the end of the ram 25. With the trigger 26 in place around the prongs, the prongs cannot flex outward and therefore the prongs retain the ram 25. Once the trigger 26 is moved upward, it no longer constrains the latch prongs. Thus, the ram 25 is free to be pushed downward by the force of the main spring 24.

At the end of injection (FIG. 4; bottom left), the ram 25 has extended past the lock out features on the latch 23 and come to rest against the flange of the pre-filled syringe 10. Ram 25 displacement is limited by its leading collar contacting the outer face of the syringe flange. After injection and when the needle 12 is removed from the injection site, the needle guard 34 extends such that the needle 12 is shrouded (FIG. 4; bottom right). Lock out clip features present on the needle guard legs interact with lockout clip features on the latch 23, preventing displacement of the needle guard 34 and providing a lockout function for sharps protection.

Epinephrine is chemically unstable in solution and it can undergo a series of complex reactions in the product including oxidation, hydrolytic and substitution reactions. Epinephrine also undergoes a series of chemical, enzymatic, and metabolic pathways upon injection into the human body.

The rates of these reactions depend on the complex interplay of light, pH, dissolved oxygen and available bisulfites. In detail:

An aqueous solution of epinephrine is sensitive to light and undergoes degradation even when subjected to natural light. Photo-stability of epinephrine is dependent on the epinephrine concentration and the presence of other formulation additives. Light is also known to catalyze the oxidation reaction of epinephrine. The photo-degradation kinetics of epinephrine appears to be faster in the presence of bisulfite than in its absence. Therefore, epinephrine must be protected from light or under filtered light during compounding.

Epinephrine is oxidized rapidly by molecular oxygen and other oxidizing agents to produce colour forming oxidized species. This discoloration is pharmaceutically unacceptable and appropriate antioxidants are necessary to stabilize epinephrine formulations. one particularly suitable antioxidant is sodium metabisulfite.

Oxidation appears to be catalyzed by light and hence protection from light is required. The rate of oxidation also increases with increasing pH of the formulation. However, formulating at low pH is not a viable option because the rate of another degradation pathway, i.e., racemization, increases with decreasing pH. In conclusion, stabilization of epinephrine in the formulation and avoiding formation of coloured impurities requires optimization of pH, lack of exposure to light and oxygen during manufacturing and in the product, and incorporation of an antioxidant such as sodium metabisulfite (SMBS). SMBS is also known to react readily with epinephrine to form sulfonated impurities. Therefore, the SMBS level is optimized to ensure satisfactory product attributes.

Sodium metabisulfite, by preferential oxidation, protects epinephrine from oxidation by molecular oxygen. The preferential oxidation yields sulfate species that result in a pH decrease as bisulfate is a stronger acid than bisulfite. This reaction has an indirect implication on epinephrine stability as the pH of the formulations decreases on storage as a result of sulfite oxidation.

The mechanism of sulfite (or bisulfite) oxidation depends on bisulfite concentration. Therefore, an optimum concentration of bisulfite is selected for use as antioxidant such that it predominantly reacts only with dissolved oxygen as an antioxidant, but minimally contribute to sulfonation reactions.

While bisulfite protects epinephrine from oxidation, it reacts with epinephrine itself to form a pharmacologically inactive sulfonate. The rate of sulfonation reaction increases with an increase in pH. As bisulfite is used as an antioxidant in formulations of epinephrine, care is taken to adjust the concentration of drug, antioxidant, and pH to an optimum value to ensure maximum stability.

Considering all these competing reactions that depend on pH, it is imperative to incorporate a buffer (in the pH range of 2-5, and more specifically 3-4) into the epinephrine solution to enhance its chemical stability. The buffer is preferably a carboxylic acid and more preferably a dicarboxylic acid. Dicarboxylic acids are characterized by two functional carboxyl groups and include linear saturated dicarboxylic acids such as oxalic acid, malonic acid, succinic acid, glutaric acid, adipic acid, pimelic acid and suberic acid, branched-chain dicarboxylic acids, unsaturated dicarboxylic acids such as maleic acid and fumaric acid and substituted dicarboxylic acids such as malic acid, aspartic acid, glutamic acid and tartaric acid. Among the various dicarboxylic acids that can act as buffer in the pH range between 2 and 5, tartaric acid is preferred to buffer the epinephrine formulation, because tartaric acid is a bicarboxylic acid with $pK_a$ values of 3.03 and 4.37 A carboxylic acid exerts a strong buffering capacity within the pH range of $pK_a \pm 0.5$ units and less so at $pK_a \pm 1.0$. Based on this, tartaric acid exerts strong buffering capacity in the desired pH range between 2.5 (3.03−0.50) and 4.9 (4.37+0.50). Further, epinephrine has been reported to form salt with tartaric acid as epinephrine bitartrate.

The concentration of the tartrate buffer in the pharmaceutical composition for administration to pediatric patients is between 0.3 and 1 mg/ml, preferably between 0.4 mg/ml and 0.9 mg/ml, more preferably between 0.5 mg/ml and 0.8 mg/ml and most preferably it is 0.69 mg/mL. The concentration of the tartrate buffer in the pharmaceutical composition for administration to adult patients is between 0.8 and 2 mg/ml, preferably between 1.0 mg/ml and 1.6 mg/ml, more preferably between 1.2 mg/ml and 1.5 mg/ml and most preferably it is 1.38 mg/mL.

As discussed earlier, addition of an antioxidant such as SMBS as is required for epinephrine stability. However, excess SMBS itself will react with epinephrine through sulfonation reaction. In addition, only 0.25 mM of SMBS is required to consume all (0.25 mM) the dissolved oxygen in water at atmospheric temperature and pressure. Hence, for optimum stability of epinephrine, it is useful to reduce the SMBS concentration that is added. As a result of this reduction in SMBS concentration, less epinephrine sulfonic acid would be formed. Hence, the concentration of sodium metabisulfite in the pharmaceutical composition is 0.5 to 1.8 mg/ml, preferably 0.7 to 1.5 mg/ml, more preferably 1.0 to 1.4 mg/ml and most preferably it is 1.2 mg/ml.

In one embodiment, the pharmaceutical composition comprises epinephrine, sodium chloride, sodium metabisulfite, sodium tartrate dihydrate and water for injection and the pH is adjusted with hydrochloric acid. In one embodiment, the pharmaceutical composition for administration to adults comprises 1 mg/ml epinephrine, 100 mM sodium chloride, 1.2 mg/ml sodium metabisulfite, 1.38 mg/ml sodium tartrate dihydrate and water for injection and the pH is adjusted with hydrochloric acid. In one embodiment, the pharmaceutical composition for administration to pediatric patients comprises 0.5 mg/ml epinephrine, 100 mM sodium chloride, 1.2 mg/ml sodium metabisulfite, 0.69 mg/ml sodium tartrate dihydrate and water for injection and the pH is adjusted with hydrochloric acid.

As a summary, the pre-filled syringe according to the invention comprises epinephrine and a buffer configured to buffer in a pH range between 3 and 4 to minimize degradation reactions and to thereby keep the composition stable, and a needle adhered to a container by means of a urethane methacrylate acrylic light cure adhesive configured to keep above defined pull out resistance stable. As a synergetic effect, the stable composition avoids more severe attacks of the composition on the adhesive and the stable adhesive avoids more severe attacks of the surrounding oxygen on the composition. Consequently, the shelf life of the pre-filled syringe is greatly increased.

Figure 5:
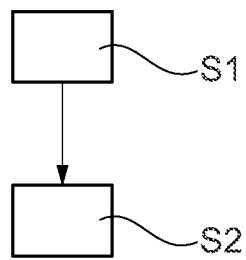
FIG. 5 shows a schematic overview of steps of a method of administering a pharmaceutical composition with an auto-injector device.

FIG. 5 shows a schematic overview of steps of a method of administering a pharmaceutical composition with an auto-injector device 20. The method comprises the following steps:

In a first step S1, providing an auto-injector device 20 comprising a syringe and a firing mechanism 21. The syringe comprises a needle 12 and a container 11. The container 11 is filled with a pharmaceutical composition comprising epinephrine, a buffer, and water. The buffer is configured to buffer in a pH range between 3 and 4. The needle 12 is adhered to the container 11 by means of a urethane methacrylate acrylic light cure adhesive, which is configured to provide a pull out resistance of the needle 12 relative to the container 11 which is greater than 60 N after 90 days exposure to the pharmaceutical composition at 40° C. and 75% RH.

In a second step S2, activating the firing mechanism 21 to expel the pharmaceutical composition from the syringe and to inject it into a subject.

Figure 6:
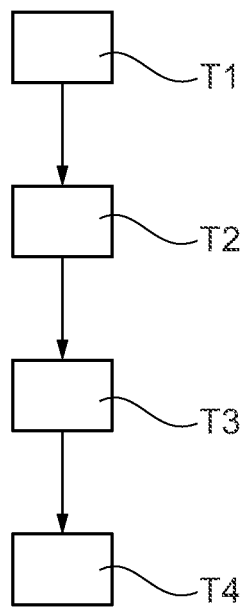
FIG. 6 shows a schematic overview of steps of a manufacturing method for an auto-injector device.

FIG. 6 shows a schematic overview of steps of a manufacturing method for an auto-injector device 20. The method comprises the following steps:

In a first step T1, manufacturing a pharmaceutical composition comprising epinephrine, a buffer, and water. The buffer is configured to buffer in a pH range between 3 and 4. The manufacturing method for the pharmaceutical composition may be described as follows. About 100 L of water for injection (WFI) is dispensed into a 100 L stainless steel tank. To reduce the dissolved oxygen content, degassed WFI is used. Degassing was done by vacuum for 45 min and then sparged with nitrogen gas at a minimum of 4 L/min for about 2 h and then finally under vacuum for 45 min. About 80% of the batch weight of degassed WFI is dispensed from the stainless steel tank into a compounding vessel. The excipients (sodium chloride, sodium metabisulfite, sodium tartrate, and HCl) are dispensed into the compounding vessel and mixed to yield a clear solution. Then, the diluted solution (DS) is dispensed into the compounding vessel and mixed for DS dissolution. The pH is adjusted to the target pH value using HCl. The remaining amount of WFI is added to reach the final target weight.

In a second step T2, sterilizing the pharmaceutical composition. The sterilization relies on the input of sufficient energy to be lethal to any potential microbial contamination. The used methods may comprise heat and irradiation. The pharmaceutical composition or epinephrine bulk solution can be sterilized by continuous filtration through two (redundant) sterile 0.22 μm PVDF filters during filling. The container 11 and closures are "ready to use" components i.e., sterilized by gamma irradiation.

In a third step T3, filling the pharmaceutical composition into a barrel or container 11 of a syringe. The syringe further comprises a needle 12 made of stainless steel 316 L. The needle 12 is adhered to a rubber stopper put into an opening of the container 11 by means of a urethane methacrylate acrylic light cure adhesive as e.g. Loctite 3345. The adhesive is configured to provide a pull out resistance of the needle 12 relative to the container 11 which is greater than 60 N after 90 days exposure to the pharmaceutical composition at 40° C. and 75% RH. The pull out resistance may also be defined to be between 80 N and 95 N after 90 days exposure to the pharmaceutical composition at 40° C. and 75% relative humidity (RH).

In a fourth step T4, assembling the syringe into an auto-injector device 20 which comprises a firing mechanism 21. The firing mechanism 21 is configured to expel the pharmaceutical composition from the syringe and to inject it into a subject.

In other words, the manufacturing of the pharmaceutical composition starts with weighing degassed water for injection into a compounding tank and dissolving excipients. Then, to the excipient solution, dispensed amount of API is added followed by predetermined quantity of HCl. After completion of dissolution, pH of the solution is adjusted to the target pH of between 3 and 4 with further amount of HCl. The compounded bulk solution is continuously sterile filtered and filled into the container 11 or the barrel of the pre-filled syringe 10, which is then sealed with a rubber stopper under vacuum.

As epinephrine degradation may be facilitated by the presence of oxygen in a headspace of the syringe barrel or container 11, this risk may be reduced by adjusting a stopper placement to an optimum stopper height and lower headspace. The term "headspace" refers to the gas space above the product in a container. The headspace gas may be manipulated in order to reduce the amount of oxygen present therein. In detail:

During a filling process, a needle 12 goes into the syringe and fills the syringe with 1.04 mL of formulation. After filling, the needle 12 is removed and appropriate vacuum setting is reached and the desired dwell time has passed, the insertion rod pushes the stopper into the top of the syringe barrel to a specified position. The stopper height relies on the fill volume and the applied vacuum pressure. The stopper placement is checked via manual and automated inspection. The liquid level in the syringe relative to the syringe top flange depends on the fill volume and internal diameter (ID) of the syringe. The inner diameter of the syringe cartridge is preferably between 6.25 mm to 6.45 mm, nominal 6.35 mm. The tolerance in the precise volume fill is preferably below 0.03 ml. The opening is closed after the filling by an inserted rubber stopper. Vacuum is supplied to pull the stopper thru the syringe barrel from flange to top of the fill volume. The stopper is inserted into the syringe at the desired vacuum pressure setpoint within the following range for example, 28-44 mbar.

The container may be made of glass, containing a chlorobutyl elastomeric rubber stopper as container closure system for product, and the needle may be made of stainless steel 316 L.

The dose accuracy or delivered dose is mainly influenced by the headspace z and the stopper height (i.e., plunger position). The stopper height, distance between stopper rear face and the end face of the syringe's flange, relies on the syringes tolerance in length, the syringe ID, the tolerance in stopper length and on the applied vacuum pressure (ie lower vacuum pressure setpoint corresponds to a stronger vacuum) and dwell time at the stopper insertion process The syringe length tolerance shall be between 0.2 to 1 mm, preferably equal or below 0.5 mm. The tolerance in stopper length shall be between 0.2 to 0.8 mm, preferably equal or below 0.4 mm and the tolerance in the stopper width is 0.0-0.2 mm.

After insertion of the stopper air pressure is returned to atmospheric pressure and the stopper moves forward to contact the fluid with leaving a headspace z above the liquid level. In an example contributors to a variation in dose delivered could be plunger position (gap between ram/plunger end face and stopper rear face), variation in ram/plunger length, plunger mechanical dynamic and an effective displacement of the stopper due to an air bubble at the headspace z. Of these contributors effective displacement of the stopper due to an air bubble is the largest contributor.

To compensate headspace volume associated with potential bubbles and deliver at least 0.25 ml, preferably more than 0.28 ml of epinephrine formulation and a nominal volume of 1.04 ml is filled into the syringe at a vacuum pressure setpoint of 28-44 mbar (ie, a higher vacuum pressure set point corresponds to a weaker vacuum and results in smaller stopper height and a greater deliverable volume). Thus a nominal dose of 0.3 ml, preferably between 0.28 ml to 0.34 ml of the pharmaceutical epinephrine composition/formulation is injected.

A first batch of 616 auto-injectors containing epinephrine at a concentration of 1 mg/mL was tested with respect to the volume of epinephrine that was delivered after actuating a device. The mean delivered volume was 0.299 ml with a Standard Deviation (Std Dev) of less than 0.015 ml (95% Upper and Lower Confidence Interval for Mean).

A second batch of 1197 auto-injectors containing epinephrine at a concentration of 0.5 mg/mL was tested with respect to the volume of epinephrine that was delivered after actuating a device. The mean delivered volume was 0.302 ml with a Standard Deviation (Std Dev) of less than 0.010 ml (95% Upper and Lower Confidence Interval for Mean).

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

Example 1 represents an example formulation composition of the pharmaceutical composition comprised in the pre-filled syringe for epinephrine injection according to the invention.

| Ingredients | Function | Adult | Junior |
|---|---|---|---|
| Epinephrine | Active | 1.0 mg/mL | 0.5 mg/mL |
| Sodium Chloride | Tonicity adjustment | 6 mg/mL | 6 mg/mL |
| Sodium Metabisulfite | Antioxidant | 1.2 mg/mL | 1.2 mg/mL |
| Sodium Tartrate dihydrate | Buffer | 1.38 mg/mL | 0.69 mg/mL |
| Hydrochloric Acid | pH adjuster | pH 2.2-5.0 | pH 2.2-5.0 |
| Water for Injection | Vehicle | Q.S | Q.S |

Further Embodiments

1. A pre-filled syringe (10) comprising a container (11) and a needle (12),
   wherein the container (11) is filled with a pharmaceutical composition comprising epinephrine, a buffer, and water;
   wherein the buffer is configured to buffer in a pH range between 3 and 4,
   wherein the needle (12) is adhered to the container (11) by means of a urethane acrylate or urethane methacrylate acrylic light cure adhesive, and
   wherein the urethane acrylate or urethane methacrylate acrylic light cure adhesive is configured to provide a pull out resistance of the needle (12) relative to the container (11) which is greater than 60 N after 90 days exposure to the pharmaceutical composition at 40° C. and 75% RH.
2. Pre-filled syringe (10) according to embodiment 1, wherein the needle (12) is made from high corrosion resistance steel comprising 15 to 20% Cr, 8 to 16% Ni and 1 to 4% Mo.
3. Pre-filled syringe (10) according to embodiment 1, wherein the needle (12) is made from high corrosion resistance steel comprising 15 to 25% Cr, 20 to 30% Ni and 3 to 6% Mo.
4. Pre-filled syringe (10) according to claim 1, wherein the container (11) contains between 0.95 ml and 1.07 ml, and preferably between 1.04 and 1.07 ml of the pharmaceutical composition.
5. Pre-filled syringe (10) according to one of the preceding embodiments, wherein the needle (12) has an inner diameter (ID) between 0.39 to 0.53 mm.
6. Pre-filled syringe (10) according to one of the preceding embodiments, wherein the buffer is a bicarboxylic acid.
7. Pre-filled syringe (10) according to one of the preceding embodiments, wherein the buffer is a tartrate salt.
8. Pre-filled syringe (10) according to one of the preceding embodiments, wherein the buffer is sodium tartrate dihydrate.
9. Pre-filled syringe (10) according to the preceding embodiment, wherein the sodium tartrate dihydrate content is between 1.0 and 1.6 mg/mL for adult patients or between 0.5 and 0.8 mg/mL for pediatric patients.
10. Pre-filled syringe (10) according to embodiment (, wherein the sodium tartrate dihydrate content is about 1.38 mg/mL for adult patients or about 0.69 mg/mL for pediatric patients.
11. Pre-filled syringe (10) according to one of the preceding embodiments, wherein the pharmaceutical composition further comprises an antioxidant,
    wherein the antioxidant is sodium metabisulfite, and
    wherein the sodium metabisulfite content in the pharmaceutical composition is about 1.2 mg/mL.
12. Pre-filled syringe (10) according to one of the preceding embodiments, wherein the pharmaceutical composition further comprises a pH adjuster and a tonicity adjuster,
    wherein the pH adjuster is a hydrochloric acid,
    wherein the tonicity adjuster is a sodium chloride, and
    wherein the epinephrine content is between 0.9 and 1.1 mg/mL for adult patients or between 0.4 and 0.6 mg/mL for pediatric patients.

13. An auto-injector device (20), comprising:
    a pre-filled syringe (10) according to one of the preceding embodiments, and
    a firing mechanism (21),
    wherein the firing mechanism (21) is configured to expel a pharmaceutical composition from the pre-filled syringe (10) and to inject it into a subject.
14. Auto-injector device (20) according to the preceding embodiment, wherein the pressure during injection into the subject is in a range of 100 to 4000 psi.
15. Auto-injector device (20) according to one of the preceding embodiments, wherein the pre-filled syringe (10) provides about 1 mL of the pharmaceutical composition and the auto-injector device (20) is configured to deliver about 0.3 ml of the pharmaceutical composition during a single injection in below 0.5 sec.
16. A manufacturing method for an auto-injector device (20), comprising the following steps:
    manufacturing a pharmaceutical composition comprising epinephrine, a buffer, and water, wherein the buffer is configured to buffer in a pH range between 3 and 4,
    sterilizing the pharmaceutical composition,
    filling the pharmaceutical composition in a container (11) of a pre-filled syringe (10) according to one of the preceding embodiments 1 to 12, and
    assembling the pre-filled syringe (10) into an auto-injector device (20) comprising a firing mechanism (21), wherein the firing mechanism (21) is configured to expel the pharmaceutical composition from the pre-filled syringe (10) and to inject it into a subject.
17. Manufacturing method according to the preceding embodiment, wherein the manufacturing of the pharmaceutical composition comprises the following steps:
    preparing a solution comprising the buffer and an anti-oxidant,
    adding a pH adjuster to adjust a pH range of the solution between 2.5 and 4.3,
    adding epinephrine, and
    adding a pH adjuster to adjust a pH range of the solution comprising epinephrine between 3 and 4.
18. Manufacturing method according to one of the preceding embodiments, wherein the pH adjuster is added to adjust a pH value of the solution comprising epinephrine to about 3.4.
19. Manufacturing method according to one of the preceding embodiments, wherein the manufacturing of the pharmaceutical composition comprises the further steps of
    degassing water, and
    adding the degassed water to the solution comprising epinephrine,
    wherein the degassing of water comprise the steps of:
    a) subjecting water to vacuum,
    b) sparging the water with nitrogen gas, and
    c) again subjecting the water to vacuum.
20. Manufacturing method according to the preceding embodiment, wherein the water is subjected to vacuum for about 45 minutes in step a) and in step c).
21. Manufacturing method according to one of the preceding embodiments, wherein the water is sparged with nitrogen gas at a minimum of 4 L/min for about 120 minutes.
22. Manufacturing method according to one of the preceding embodiments, wherein the sterilizing of the pharmaceutical composition comprises an aseptic filtration.
23. Manufacturing method according to the preceding embodiment, wherein aseptic filtration is done at room temperature by means of a polyvinylidenfluoride filter.
24. Manufacturing method according to the preceding embodiment, wherein the filter has a pore size in the range of 0.1 to 0.3 μm.
25. Manufacturing method according to one of the preceding embodiments, wherein the filling of the pharmaceutical composition in the pre-filled syringe (10) is done through an opening, wherein the opening is closed after the filling by a stopper, and a flange surrounding the opening is subjected to vacuum forcing air below the stopper to be removed from the syringe.
26. A method of administering a pharmaceutical composition with an auto-injector device (20), comprising the following steps:
    providing an auto-injector device (20) according to one of the preceding embodiments, and
    activating the firing mechanism (21) of the auto-injector device (20) to expel a pharmaceutical composition from a pre-filled syringe (10) of the auto-injector device (20) and to inject it into a subject.
27. Method according to the preceding embodiment, wherein the pharmaceutical composition is for the treatment of an anaphylactic event.

The invention claimed is:
1. A manufacturing method for an auto-injector, the manufacturing method comprising:
    manufacturing a pharmaceutical composition, the pharmaceutical composition comprising epinephrine, a buffer, and water, wherein the pharmaceutical composition has a pH ranging between 3 and 4;
    sterilizing the pharmaceutical composition;
    adhering a stainless steel needle to a glass container with an adhesive, wherein the adhesive comprises at least one of a urethane acrylate adhesive or a urethane methacrylate adhesive;
    filling the glass container with at least 1 mL of the pharmaceutical composition to form a pre-filled container; and
    assembling the pre-filled container into the auto-injector, wherein the auto-injector is for single use injection and comprises a firing mechanism, wherein the firing mechanism is configured to expel only a single injection of about 0.3 mL of the at least 1 mL of the pharmaceutical composition from the pre-filled container, and the firing mechanism is configured to expel the single injection in less than 0.5 seconds.
2. The manufacturing method of claim 1, wherein the manufacturing of the pharmaceutical composition comprises:
    preparing a solution comprising the buffer and an anti-oxidant;
    adding a pH adjuster to adjust a pH of the solution to a range between 2.5 and 4.3;
    adding the epinephrine; and
    adding, after adding the epinephrine, the pH adjuster or another pH adjuster to adjust a pH of the solution comprising the epinephrine to a range between 3 and 4.
3. The manufacturing method of claim 2, wherein the pH adjuster or the other pH adjuster is added to adjust the pH of the solution comprising the epinephrine to about 3.4.
4. The manufacturing method of claim 1, wherein the sterilizing of the pharmaceutical composition comprises performing an aseptic filtration.
5. The manufacturing method of claim 4, wherein performing the aseptic filtration occurs at room temperature with a polyvinylidenfluoride filter.

6. The manufacturing method of claim 5, wherein the polyvinylidenfluoride filter has a pore size ranging between 0.1 [tm and 0.3 [tm.

7. The manufacturing method of claim 1, wherein the glass container is filled with the pharmaceutical composition through an opening, and wherein the opening is closed after the filling by a stopper using a vacuum stoppering technique.

8. The manufacturing method of claim 1, wherein the stainless steel needle comprises 15 to 20% Cr, 8 to 16% Ni, and 3 to 4% Mo.

9. The manufacturing method of claim 1, wherein the stainless steel needle comprises 15 to 20% Cr, 20 to 30% Ni, and 3 to 6% Mo.

10. The manufacturing method of claim 1, wherein the buffer comprises at least one of bicarboxylic acid, tartrate salt, or sodium tartrate dihydrate.

11. The manufacturing method of claim 1, wherein the pharmaceutical composition further comprises an antioxidant.

12. The manufacturing method of claim 11, wherein the antioxidant comprises sodium metabisulfite.

13. The manufacturing method of claim 1, wherein the firing mechanism is configured to expel the pharmaceutical composition from the pre-filled container at a pressure ranging between 100 psi and 4000 psi.

14. The manufacturing method of claim 1, wherein, after the adhesive is exposed to the pharmaceutical composition for 90 days at 40° C. and 75% relative humidity, the adhesive is configured to resist a pull out force of between 30 N and 100 N applied to at least one of the stainless steel needle or the glass container.

15. The manufacturing method of claim 1, wherein the firing mechanism is configured such that at least about 0.7 mL of the at least 1 mL of the pharmaceutical composition remains in the auto-injector after the single injection.

16. The manufacturing method of claim 15, wherein the auto-injector is configured to prevent the at least about 0.7 mL of the at least 1 mL of the pharmaceutical composition from being expelled from the pre-filled container.

17. The manufacturing method of claim 16, wherein the firing mechanism comprises a ram configured to expel the pharmaceutical composition from the pre-filled container, and wherein, after the single injection, the ram is configured to rest against the pre-filled container to prevent another injection of the pharmaceutical composition from the pre-filled container.

18. A manufacturing method for an auto-injector, the manufacturing method comprising:
    degassing water comprising:
        subjecting the water to a vacuum to form vacuumed water,
        sparging the vacuumed water with nitrogen gas to form sparged water, and subjecting the sparged water to a vacuum to form degassed water;
    manufacturing a pharmaceutical composition, the pharmaceutical composition comprising epinephrine, a buffer, and the degassed water, wherein the pharmaceutical composition has a pH ranging between 3 and 4;
    sterilizing the pharmaceutical composition;
    adhering a stainless steel needle to a glass container with an adhesive, wherein the adhesive comprises at least one of a urethane acrylate adhesive or a urethane methacrylate adhesive;
    filling the glass container with at least 1 mL of the pharmaceutical composition to form a pre-filled container; and
    assembling the pre-filled container into the auto-injector, wherein the auto-injector comprises comprising a firing mechanism, wherein the firing mechanism is configured to expel the pharmaceutical composition from the pre-filled container.

19. The manufacturing method of claim 18, wherein the water is subjected to the vacuum for about 45 minutes.

20. The manufacturing method of claim 18, wherein the vacuumed water is sparged with the nitrogen gas at a minimum of 4 L/min for about 120 minutes.

21. The manufacturing method of claim 18, wherein, after the adhesive is exposed to the pharmaceutical composition for 90 days at 40° C. and 75% relative humidity, the adhesive is configured to resist a pull out force of between 30 N and 100 N applied to at least one of the stainless steel needle or the glass container.

22. The manufacturing method of claim 18, wherein the firing mechanism is configured to expel about 0.3 mL of the pharmaceutical composition from the pre-filled container in less than 0.5 seconds-during a single injection.

23. The manufacturing method of claim 18, wherein the sterilizing of the pharmaceutical composition comprises performing an aseptic filtration.

24. The manufacturing method of claim 18, wherein the glass container is filled with the pharmaceutical composition through an opening, and wherein the opening is closed after the filling by a stopper using a vacuum stoppering technique.

25. The manufacturing method of claim 18, wherein the firing mechanism is configured to expel the pharmaceutical composition from the pre-filled container at a pressure ranging between 100 psi and 4000 psi.

26. The manufacturing method of claim 18, wherein the buffer comprises at least one of bicarboxylic acid, tartrate salt, or sodium tartrate dihydrate.

27. The manufacturing method of claim 18, wherein the pharmaceutical composition further comprises an antioxidant.

* * * * *